United States Patent [19]

Kunkel

[11] Patent Number: 5,736,584
[45] Date of Patent: Apr. 7, 1998

[54] INSECT REPELLANT COMPRISING PRICKLY PEAR CACTUS EXTRACT

[76] Inventor: Dick Kunkel, 8505 Directors Row, Dallas, Tex. 75247

[21] Appl. No.: 734,529

[22] Filed: Oct. 21, 1996

[51] Int. Cl.[6] ............................. A01N 65/00; A61K 35/78
[52] U.S. Cl. .............. 514/919; 424/195.1; 424/DIG. 10
[58] Field of Search ...................... 424/195.1, DIG. 10; 514/919

[56] References Cited

U.S. PATENT DOCUMENTS

| | | | |
|---|---|---|---|
| 2,778,797 | 1/1957 | Dickenson | 210/2 |
| 2,845,363 | 7/1958 | Gutzeit | 106/205 |
| 3,227,616 | 1/1966 | Van Wessem et al. | 167/91 |
| 4,042,720 | 8/1977 | Forkner | 426/573 |
| 4,361,554 | 11/1982 | Saunders | 424/195 |
| 4,617,188 | 10/1986 | Page et al. | 424/148 |

OTHER PUBLICATIONS

Grainge et al. *Handbook of Plants with Pest–Control Properties*. John Wiley & Sons. pp. xiii, 195, 196. 1988.

*Primary Examiner*—S. Mark Clardy
*Attorney, Agent, or Firm*—Charles D. Gunter, Jr.

[57] ABSTRACT

An insect repelling composition includes a mineral oil based carrier and, as an active ingredient, an insect repelling amount of cactus extract made from the leaves and stem of the Prickly Pear cactus. A pest repellant formulation can be prepared by combining an oil based carrier with an insect repelling amount of cactus extract and applying the repellant to the skin, hair or fur of a mammal.

8 Claims, No Drawings

INSECT REPELLANT COMPRISING PRICKLY PEAR CACTUS EXTRACT

BACKGROUND OF THE INVENTION

1. Field of the Invention

The present invention relates generally to repellant compositions for repelling insects from a surface and, more specifically, to repellant compositions for repelling small blood feeding pests from the skin, hair or fur of mammals.

2. Description of the Prior Art

A variety of insect rebuffer/repellant compositions are known in the prior art for repelling small blood feeding pests from the skin, hair or fur of mammals. The term "insect", as used in this disclosure, is intended to encompass such small blood feeding pests as mosquitoes, fleas, ticks, black flies, gnats, and the like. Many of the prior art compositions are either relatively expensive to manufacture, incorporating various exotic ingredients, or contain ingredients which are potentially toxic or at the least irritating to the human epidermis or other surfaces of application. Certain of the compounds used in formulating the prior art compositions are environmentally hazardous and present environmental disposal problems.

U.S. Pat. No. 4,816,256, issued Mar. 28, 1989, entitled "Mosquito Repellant Compositions" shows a typical prior art composition comprising an active agent and an oil soluble, water insoluble acrylate polymer having specific solubility parameters.

U.S. Pat. No. 4,547,360, issued Oct. 15, 1985, shows a composition for repelling pests which includes, as an active ingredient, cyano(3-phenoxyphenyl) methyl-4-chloro-alpha-(1 methylethyl) benzeneacetate.

U.S. Pat. No. 4,264,594, issued Apr. 27, 1981, shows an insect repellant which includes, as an active ingredient, the carboxamide of azepine which contains an alicyclic moiety.

U.S. Pat. No. 5,093,326, issued Mar. 3, 1992, shows an insect repellant composition which includes the ozonide of an unsaturated hydrocarbon. Other examples of suitable unsaturated hydrocarbons listed include natural and synthetic steroids, alkenes and their substituted derivatives.

The above references are merely intended to be representative of the general nature of prior art compositions in the insect repellant/rebuffer field which utilize fairly exotic active ingredients which are typically potential skin irritants, toxicants, environmental pollutants, or the like.

A need exists for an insect repellant/rebuffer which is formulated from relatively simple, easily obtainable components and which is economical to manufacture.

A need also exists for such a repellant composition which contains, as the active ingredient, a naturally occurring non-toxic and environmentally friendly component.

A need also exists for such a rebuffer/repellant composition which utilizes as the active ingredient thereof a non-toxic commodity which is naturally occurring in the environment and thus extremely economical to obtain and prepare for use when formulated in a suitable carrier at an effective repellant concentration.

SUMMARY OF THE INVENTION

The repellant compositions of the invention can be used to repel insects and other pests from a surface and include, as an active ingredient, an insect repelling amount of cactus extract and a carrier, excipient or diluent suitable for application to the surface.

Preferably, the insect repelling composition is intended for use on the human skin and includes an oil based carrier and, as an active ingredient, an insect repelling amount of cactus extract. The preferred oil based carrier is a mineral oil and the cactus extract is prepared from parts of the Prickly Pear cactus plant. The compositions can also incorporate traditional surfactants, coupling agents, emollients, and the like. In a particularly preferred composition, the cactus extract is present in a major amount, in the range from about 20 to 60% by weight, most preferably about 40% by weight, based on the total weight of insect repelling composition.

In the method of the invention, small blood feeding pests are repelled from the skin, hair or fur of a mammal by applying a pest repellant amount of a repellant which is formulated by combining an oil based carrier with an insect repelling amount of cactus extract to the skin, hair or fur of the mammal. Preferably, the repellant is formulated by combining an oil based carrier with an insect repelling amount of cactus extract where the cactus extract is prepared by boiling parts of the Prickly Pear cactus to produce a liquid containing solids. The liquid is separated to form a liquid extract from the remaining solids produced by the boiling and the pH of the resulting extract is adjusted within the range from about 4 to 6. The cactus extract is present in the repellant so formulated in the range from about 20 to 60% by weight, preferably about 40% by weight, based on the total weight of the repellant.

Additional objects, features and advantages will be apparent in the written description which follows.

DETAILED DESCRIPTION OF THE INVENTION

The insect rebuffer/repellant compositions of the invention contain, as an active ingredient, and as a major proportion of the compositions, an all natural ingredient. This all natural ingredient is cactus extract made from the leaves and stems of the Prickly Pear or Opuntia family of cactus. This family of cactus is widespread in the Southwestern portion of the United States. "Nopalitos", namely the tender Prickly Pear stems and leaves, are a traditional vegetable in Mexico and a specialty vegetable in the United States. The vegetable is not a true leaf but rather the young, rapidly growing flattened stems or cladodes of the Prickly Pear cactus. The vestigial true leaves, often subtended by spines, are present in the early stages of Nopalito growth, but usually begin to fall off by the time the Nopalitos reach commercial size. Good quality Nopalitos are fresh looking, turgid with a brilliant green color. After trimming and chopping, the Nopalitos may be eaten as a fresh or cooked vegetable, resembling green beans somewhat in flavor.

The leaves and stems of the Prickly Pear cactus are mostly water (92%) and carbohydrates including fiber (4–6%) with some protein (1–2%) and minerals, including principally calcium (1%). They also contain moderate amounts of Vitamin C and the Vitamin A precursor beta-carotene. Surprisingly, for purposes of the present invention, cactus extract prepared according to the herein described process has been found to comprise a form of a natural "rodene" in liquid form, i.e., a composition which acts to repel mosquitoes and other small blood feeding pests of the skin, hair or fur of mammals. Most rodene compositions occur naturally only in solid form, e.g. dry powders, which must then be dissolved or further processed.

In the first step of the method of the invention, an insect rebuffer/repellant composition is formulated by combining, as an active ingredient, an insect repelling amount of cactus extract with a carrier, excipient or diluent suitable for application to the surface being treated. The cactus extract is preferably prepared by producing a pulp of the leaves and stem from a cactus such as the Prickly Pear (Opuntia) cactus. The leaves and stems of the cactus are boiled at a rolling boil in water at a ratio of about 1 pound of Prickly Pear cactus parts to 1¾ gallons of water. The cactus parts are boiled at approximately 212° F., at sea level, or at the boiling point of the carrier liquid, until there is a definite color change in the solid material of the Prickly Pear, which typically occurs after about 3 hours. After allowing the juice to cool, a preservative, such as citric acid, is added to the liquid-solid slurry in an amount in the range from about 0.1 to 3.0% by volume of the slurry. The pH of the slurry should be between about 4–6, preferably between about 4.5 to 5. If the pH of the slurry is too high, citric acid is added in a sufficient amount to bring the pH down to the proper level. The fibrous solids are then separated from the liquid extract by screening, filtering, centrifuging, pressing, or other suitable techniques, leaving behind the liquid extract.

The carrier, excipient or diluent can be any of a number of commercially available mediums, depending upon the surface to which the repellant is applied. Where the repellant is to be applied to the human epidermis, the carrier can be any of a number of non-toxic, non-irritating cosmetic type bases which will be familiar to those skilled in the cosmetic and pharmaceutical industries. By "excipient" material is meant any of various inert substances added to a pharmaceutical type prescription to give the desired consistency or form. In the preferred embodiment, the carrier or base material is an oil base, preferably refined mineral oil. The cactus extract is present in the carrier in an effective, insect repelling amount, which will typically range from about 20 to 60% by weight, preferably about 30 to 50% by weight, most preferably about 40% by weight, based on the total weight of the insect repelling composition.

The preferred compositions will also typically comprise surfactants, coupling agents, emollients, defoamers, and the like, typically employed in water-in-oil emulsions, cosmetic creams and lotions and other known topical ointments or compositions.

Any of a number of available surfactants, emollients and the like can be utilized for forming a stable emulsion. A surfactant is an organic compound consisting of two parts: (1) a hydrophobic portion, usually including a long hydrocarbon chain; and (2) a hydrophilic portion which renders the compound sufficiently soluble or dispersible in water or another polar solvent. The combined hydrophobic and hydrophilic moieties render the compounds surface active and thus able to concentrate at the interface between a surfactant solution and another phase. Suitable surfactants, coupling agents and emollients of the invention include, for example, materials selected from the group consisting of: (a) alcohol; (b) alkanolamides; (c) alkoxylated derivatives of alcohols, alkyl phenols, amines, amides, fatty acids, fatty esters and oils; (d) amine acetates and oxides; (e) aryl, alkyl, aralkyl and alkaryl sulfonates and sulfates; (f) betaine derivatives; (g) carboxylated alcohol ethoxylates; (h) esters of fatty acids, glycols, glycerols, sucrose, glucose and phosphoric acids; (i) fluorocarbon based surfactants; (j) imidazolines, imadazolines and other heterocyclic surfactants; (k) isethionates; (l) lanolin based derivatives; (m) lecithin and lecithin derivatives; (n) lignin and lignin derivatives; (o) polysaccarides, polyacrylates and polyacrylamides, and other polymeric and block polymeric surfactants; (p) protein based surfactants; (q) quaternary surfactants; (r) sarcosine derivatives; (s) silicone based surfactants; (t) soaps; (u) sorbitan derivatives; (v) sulfates and sulfonates of amines, amides, olefins, petroleum, oils, fatty acids, fatty esters, ethoxylated alcohols and ethoxylated alkyl phenols; (w) sulfosuccinates and sulfosuccinamates; (x) taurates; and (y) thio, mercapto and phorpherous derivatives.

A particularly preferred formulation of the repellant composition of the invention is given in Table 1 below.

TABLE 1

| Ingredients | % By Weight |
| --- | --- |
| Mineral oil | 45 |
| Cactus extract | 40 |
| [1]Laureth-4 (sodium laurel sulfate) | 3 |
| [2]Isopropyl myristate | 3 |
| d-Limonene (oil of citrus peel) | 5 |
| [3]Octylphenoxy polyethoxy ethanol | 3 |
| [4]Dimethicone | 1 |
|  | 100% |

[1]coupling agent
[2]emollient
[3]surfactant and coupling agent
[4]defoamer

An invention has been provided with several advantages. The repellant compositions of the invention are formulated from simple ingredients making them economical to manufacture. The active ingredient of the compositions is a naturally occurring, non-toxic and environmentally friendly extract made from the leaves and stems of the Prickly Pear cactus. The compositions of the invention are effective at rebuffing/repelling a variety of small blood feeding pests from the skin, hair and fur of various mammals including the epidermis of humans. The compositions are especially preferred for use in rebuffing/repelling mosquitoes, black flies, gnats and other airborne pests.

While the invention has been shown in only one of its forms, it is not thus limited but is susceptible to various changes and modifications without departing from the spirit thereof.

What is claimed is:

1. A repellant composition for repelling insects from a surface, the composition comprising:

as an active ingredient, an insect repelling amount of cactus extract of between about 20 to 60% by weight of the composition; and a carrier, excipient or diluent suitable for application to the surface; and an amount of d-limonene.

2. An insect repelling composition for use on the human skin, comprising:

an oil based carrier; and as an active ingredient, an insect repelling amount of cactus extract of between about 20 to 60% by weight of the composition.

3. The composition of claim 2, wherein the oil based carrier is mineral oil and the cactus extract is prepared from parts of the Prickly Pear cactus.

4. The composition of claim 2, further comprising:

a surfactant, a coupling agent and an emollient.

5. An insect repelling composition for use on the human skin, consisting essentially of:

a mineral oil based carrier;

as an active ingredient, an insect repelling amount of cactus extract, the cactus extract being present in the range from about 20 to 60% by weight, based on the total weight of insect repelling composition; and sodium laurel sulfate coupling agent, isopropyl myristate emollient, d-limonene, octylphenoxy polyethoxy ethanol surfactant and dimethicone defoamer.

6. A method for repelling small blood feeding pests from the skin, hair or fur of a mammal, the method comprising the steps of:

applying a pest repellant amount of a repellant which is formulated by combining an oil based carrier with an insect repelling amount of cactus extract of between about 20 to 60% by weight of the repellant to the said skin, hair or fur.

7. A method for repelling small blood feeding pests from the skin, hair or fur of a mammal, the method comprising the steps of:

applying a pest repellant amount of a repellant to the said skin, hair or fur, the pest repellant being formulated by:

combining an oil based carrier with an insect repelling amount of cactus extract, the cactus extract being prepared by boiling parts of the Prickly Pear cactus to produce a liquid containing solids, separating a liquid extract from the remaining solids produced by the boiling and adjusting the pH of the liquid extract within the range from about 4 to 6 with citric acid, the cactus extract being present in the repellant so formulated in the range from about 20 to 60% by weight based on the total weight of the repellant.

8. The method of claim 7, wherein the repellant is formulated by combining:

mineral oil carrier, cactus extract as the active pest repellant, sodium laurel sulfate coupling agent, isopropyl myristate emollient, d-limonene, octylphenoxy polyethoxy ethanol surfactant and dimethicone defoamer.

* * * * *